(12) United States Patent
Cho et al.

(10) Patent No.: US 7,198,804 B2
(45) Date of Patent: Apr. 3, 2007

(54) CRUDE DRUG COMPOSITION FOR PREVENTING AND TREATING GASTROINTESTINAL DYSKINETIC DISEASES

(75) Inventors: Byung Wook Cho, Seoul (KR); Mirim Jin, Seoul (KR); Hyung-Jin Jung, Seoul (KR); Sunyoung Kim, Seoul (KR)

(73) Assignee: Helixir Co., Ltd. (KR)

(*) Notice: Subject to any disclaimer, the term of this patent is extended or adjusted under 35 U.S.C. 154(b) by 451 days.

(21) Appl. No.: 10/411,093

(22) Filed: Apr. 11, 2003

(65) Prior Publication Data
US 2003/0194451 A1   Oct. 16, 2003

Related U.S. Application Data

(60) Provisional application No. 60/372,059, filed on Apr. 12, 2002.

(51) Int. Cl.
| | |
|---|---|
| *A61K 36/00* | (2006.01) |
| *A61K 36/906* | (2006.01) |
| *A61K 125/00* | (2006.01) |
| *A61K 36/258* | (2006.01) |
| *A61K 131/00* | (2006.01) |
| *A61K 129/00* | (2006.01) |
| *A61K 36/484* | (2006.01) |

(52) U.S. Cl. ............. 424/725; 424/773; 424/728; 424/775; 424/777; 424/756

(58) Field of Classification Search ............ None
See application file for complete search history.

(56) References Cited

U.S. PATENT DOCUMENTS 5,651,997 A * 7/1997 Makino et al. ............. 424/682

OTHER PUBLICATIONS intelihealth.com/IH/ihtIH/WSIHW000/9339/9735.*

* cited by examiner

*Primary Examiner*—Christopher R. Tate
*Assistant Examiner*—Melenie McCormick
(74) *Attorney, Agent, or Firm*—Anderson Kill & Olick, PC

(57) ABSTRACT

The present invention is related to a crude drug composition essentially comprising herbs of *Sinapis Semen Alba, Ginseng Radix, Zingiberis Rhizoma Siccus, Amomi Fructus, Myristicae Semen, Saussureae Radix, Cyperi Rhizoma, Magnoliae Cortex, Arecae Semen, Crataegi Fructus, Atractylodes Rhizoma Alba, Agastachis Herba, Glycyrrhiza Radix* and additionally comprising at least one herb selected from group consisting of *Polygonati Rhizoma, Artemisiae Argyi Folium, Forsythiae Fructus, Caryophylli Flos, Raphani Semen, Menthae Herba* according to the need for the prevention and treatment of gastrointestinal dyskinetic diseases and methods of using the above crude drug composition and pharmaceutical composition as prokinetic agent.

14 Claims, 5 Drawing Sheets

CRUDE DRUG COMPOSITION FOR PREVENTING AND TREATING GASTROINTESTINAL DYSKINETIC DISEASES

CROSS REFERENCE TO RELATED APPLICATION

This application claims priority to U.S. Provisional Application No. 60/372,059, filed on Apr. 12, 2002.

FIELD OF THE INVENTION

The present invention is related to a crude drug composition essentially comprising herbs of Sinapis Semen Alba, Ginseng Radix, Zingiberis Rhizoma Siccus, Amomi Fructus, Myristicae Semen, Saussureae Radix, Cyperi Rhizoma, Magnoliae Cortex, Arecae Semen, Crataegi Fructus, Atractylodes Rhizoma Alba, Agastachis Herba, Glycyrrhiza Radix and additionally comprising at least one herb selected from group consisting of Polygonati Rhizoma, Artemisiae Argyi Folium, Forsythiae Fructus, Caryophylli Flos, Raphani Semen, Menthae Herba according to the need for the prevention and treatment of gastrointestinal dyskinetic diseases and methods of using the above crude drug composition and pharmaceutical composition as prokinetic agent.

BACKGROUND OF THE INVENTION

Gastrointestinal disorders are one of the most frequently occurring diseases in present human being exposed by various unfavorable environments. Approximately 15 to 30% of adult patients suffer from various functional dyspeptic conditions, and prokinetic agents are the major prescriptions for non-ulcer type functional dyspepsia. There are a variety of prokinetic agents in the market, and many new agents are still being developed. One of the major categories of prokinetic drugs is the serotonergic agent. 90% of serotonin (5-hydroxytryptamine, 5-HT) is present in the gut, and 4 to 5% in the central nervous system. Serotonin causes the vasodilation and constriction of smooth muscle cells. Many types of serotonin receptors have been cloned and identified. Among them, those belonging to the 5-HT$_3$ and 5-HT$_4$ receptor subtypes are the most extensively studied in gastroenterology.

One of the most widely used prokinetics, cisapride, is classified with an agonist to the 5-HT$_4$ receptor, but it has been withdrawn from the market due to some patients experiencing serious cardiac arrhythmias, especially when cisapride was co-administered with inhibitors of cytochrome P450 3A4. Mosapride citrate is another widely used prokinetic drug that also works as a 5-HT$_4$ agonist. However, it also has clinically significant adverse effects on hepatic function disorder. Indeed, in the study of rodents, mosapride citrate increased the incidence of hepatocellular adenoma and thyroid follicular cell adenoma. Therefore, there has been a need for the development of new and safe prokinetic agents.

Sinapis Semen Alba is a seed of Brassica juncea CZERN. et COSS. which belongs to Cruciferae and has been used to neuralgia, rheumatism and dermatopathy.

Ginseng Radix is a root of Panax ginseng C. A. MEYER which belongs to Araliceae and contains 5.22% of ginsenoside, palmitic acid, oleic acid, linolic acid and the like, several kinds of amino acids, peptides, vitamin A, B1, B2, C and so on. It has been known to be effective for enhancing the biological response, improving the endocrine system, stimulating the metabolism and strengthening the internal organs such as heart, stomach and spleen.

Zingiberis Rhizoma Siccus is a dried rootstock of Zingiber officinale ROSC. which belongs to Zingiberaceae and contains zingiberene, phellandrene, camphene and so on. It has been used to treat for blood discharging and diarrhea.

Amomi Fructus is a fruit of Amomum xanthioides Wall. which belongs to Zingiberaceae and contains d-borneol, bornyl-acetate, linalool, nerolidol($C_{15}H_{16}O$) and so on.

Myristicae Semen is a seed of Myristica fragrans HOUTT. which belongs to Myristicaceae and contains 2–9% of essential oil such as d-camphene and $\alpha$-pinene and the like. It has a sthenia, stomachic and cardiotonic effect.

Saussureae Radix is a root of Saussurea lappa CLARKE and the same genus plants, which belongs to Compositae, and contains 0.3–3% of essential oil such as aplotaxene, $\alpha$-ionone, $\beta$-selinene, costol, phellandrene and so on. It has been used for treating diarrhea, an intestinal convulsion and dysentery, and for depressing the blood pressure.

Cyperi Rhizoma is a rootstock of Cyperus rotundus L. which belongs to Cyperaceae. It contains 1% of essential oil such as cyperol, cyperene and patchoulenone and further contains kobusone, eugenol and so on. It has been used for treating neuralgia, indigestion, headache and gynecologic diseases.

Magnoliae Cortex is a dried stem bark or a dried root bark of Magnolia officinalis REHD. et WILS. which belongs to Magnoliaceae and contains $\beta$-eudesmol, $\gamma$-eudesmol, magnolol, honokiol, alkaloid such as anonaine and so on. It has been known for alleviating of the pain and antibiotic effect.

Arecae Semen is a seed of Areca catechu L. which belongs to Palmales and contains arecaidin, guvacoline, fatty oils, arecolin, guvacin and tannin. It has been used as parasiticide and cathartic. Crataegi Fructus is a fruit of Crataegus pinnatifida BUNGE. which belongs to Rosaceae and contains crataegolic acid, malic acid, citric acid, vitamin C, tannin and saponin.

Atractylodes Rhizoma Alba is a rootstock of Atractylodes macrocephala KOIDZ. and the same genus plants of Compositae and contains 1.4% of essential oils, atractylone, atractylol and vitamin A. It is used for treating pain, gastroenteritis, edema and as hypotensive agent.

Agastachis Herba is a whole plant of Agastache rugosa (FISCH. et MEYER) which belongs to Labiatae and contains 0.28% of essential oil such as methylchavicol, anethole, anisaldehyde, $\alpha$-limonene, p-methoxy cinnamaldehyde, $\alpha$-pienene and so on. It has ataraxic, antifebrile and stomachic effect.

Glycyrrhiza Radix is a rootstock of Glycyrrhiza uralensis FISCH. which belongs to Leguminosae and contains triterpene saponin, glycyrrhizin and so on. It has been used to decrease the level of cholesterol in the blood and to treat gastroenteritis. It has been reported to have anti-inflammatory, anti-allergic and cardiotonic effect.

Polygonati Rhizoma is a rootstock of Polygonatum doratum DRUCE. which belongs to Liliaceae and contains odoraton, convallamarin, convallarin, kaempferol-glucoside, quercitol-glycoside, vitamin A and so on. It has been used to decrease the blood pressure and to treat paralysis. It has been reported to have stomachic and cardiotonic effect.

Artemisiae Argyi Folium is a dried leaf of Artemisia argyi LEVL. et VANT. and the same genus plants of Compositae and contains the essential oils such as cineol, $\beta$-caryophellen, linalool, artemisia alcohol, camphor, borneol and so on. It has been used for treating chronic gastroenteric diseases, neuralgia, diarrhea and hypertension. Furthermore, it has the antibiotic and anti-cancer effect.

*Forsythiae Fructus* is a fruit of *Forsythia koreana* NAKAI and the same genus plants of Oleaceae and contains forsythol, sterol compound, saponin, matairesinoside and so on. It has antibiotic, antiviral, stomachic and cardiotonic effect.

*Caryophylli Flos* is a flower of *Eugenia caryophyllata* THUNB. of Myrtaceae and contains essential oils such as eugenol, acetyl eugenol, β-caryophyllene, methyl-n-pentyl ketone, salicylic acid methyl, humulene, benzaldehyde, chavicol and so on. It has antibiotic and stomachic effect.

*Raphani Semen* is a seed of *Raphanus sativus* L. of Cruciferae and contains fatty oils, α-, β-hexylaldehyde, methylmercaptane and so on. It has been known to show antibiotic, antifungal and stomachic effect.

*Menthae Herba* is a whole plant or a leaf of *Mentha arvensis* var. *piperascens* MALINV. which belongs to Labiatae and contains 77–78% of menthol, 8–12% of menthone, camphene, limonene, pinene, isomenthone and a bit of tannin and rosemarinic acid. It has headache-alleviating, stomachic and intoxificating effect.

Therefore, the present inventors have endeavored to find the effective herbal formulation for enhancing gastrointestinal motility and to study the pharmacological effect of above mentioned herbal extract and its composition on gastrointestinal dyskinetic diseases.

Finally, the present inventors have found that the crude drug composition from above herbs are effective in treating and preventing gastrointestinal dyskinetic diseases.

SUMMARY OF THE INVENTION

According to one aspect, the present invention provides a pharmaceutical composition comprising a crude drug composition consisting of more than 13 herbs for prevention and treatment of gastrointestinal dyskinetic diseases.

The present invention provides a crude drug composition essentially comprising herbs of *Sinapis Semen Alba, Ginseng Radix* and *Zingiberis Rhizoma Siccus* for preventing and treating gastrointestinal dyskinetic diseases.

The present invention provides a crude drug composition essentially comprising herbs of *Amomi Fructus, Myristicae Semen* and *Saussureae Radix* for preventing and treating gastrointestinal dyskinetic diseases.

The present invention provides a crude drug composition essentially comprising herbs of *Cyperi Rhizoma, Magnoliae Cortex, Arecae Semen, Crataegi Fructus, Atractylodes Rhizoma Alba, Agastachis Herba* and *Glycyrrhiza Radix* for preventing and treating gastrointestinal dyskinetic diseases.

The present invention provides a crude drug composition essentially comprising herbs of *Sinapis Semen Alba, Ginseng Radix, Zingiberis Rhizoma Siccus, Amomi Fructus, Myristicae Semen* and *Saussureae Radix* for preventing and treating gastrointestinal dyskinetic diseases.

The present invention provides a crude drug composition essentially comprising herbs of *Sinapis Semen Alba, Ginseng Radix, Zingiberis Rhizoma Siccus, Amomi Fructus, Myristicae Semen, Saussureae Radix, Cyperi Rhizoma, Magnoliae Cortex, Arecae Semen, Crataegi Fructus, Atractylodes Rhizoma Alba, Agastachis Herba* and *Glycyrrhiza Radix* for preventing and treating gastrointestinal dyskinetic diseases.

The present invention also provides a crude drug composition additionally comprising at least one herb selected from the group consisting of *Polygonati Rhizoma, Artemisiae Argyi Folium, Forsythiae Fructus, Caryophylli Flos, Raphani Semen* and *Menthae Herba*, besides above-mentioned essential complex herbs for preventing and treating gastrointestinal dyskinetic diseases.

The present invention also provides pharmaceutical compositions comprising the above-mentioned crude drug compositions as an active ingredient in an amount effective to preventing and treating gastrointestinal dyskinetic diseases, together with a pharmaceutically acceptable carrier.

The present invention also provides a method for treating gastrointestinal dyskinetic diseases, comprising administering the pharmaceutical composition comprising the above-mentioned crude drug composition or inventive pharmaceutical composition.

The present invention also provides a use of the above-mentioned crude drug composition for the preparation of prokinetic agent for treating gastrointestinal dyskinetic diseases.

The present invention also provides a health food comprising the above mentioned crude drug composition as an active ingredient in an amount effective to preventing and improving gastrointestinal dyskinetic diseases, together with a sitologically acceptable additive.

The present invention still provides processes for preparing the above-mentioned crude drug composition.

BRIEF DESCRIPTION OF THE DRAWINGS

The above and other objects, features and other advantages of the present invention will more clearly understood from the following detailed description taken in conjunction with the accompanying drawings, in which.

DETAILED DESCRIPTION OF THE INVENTION

Figure 1:
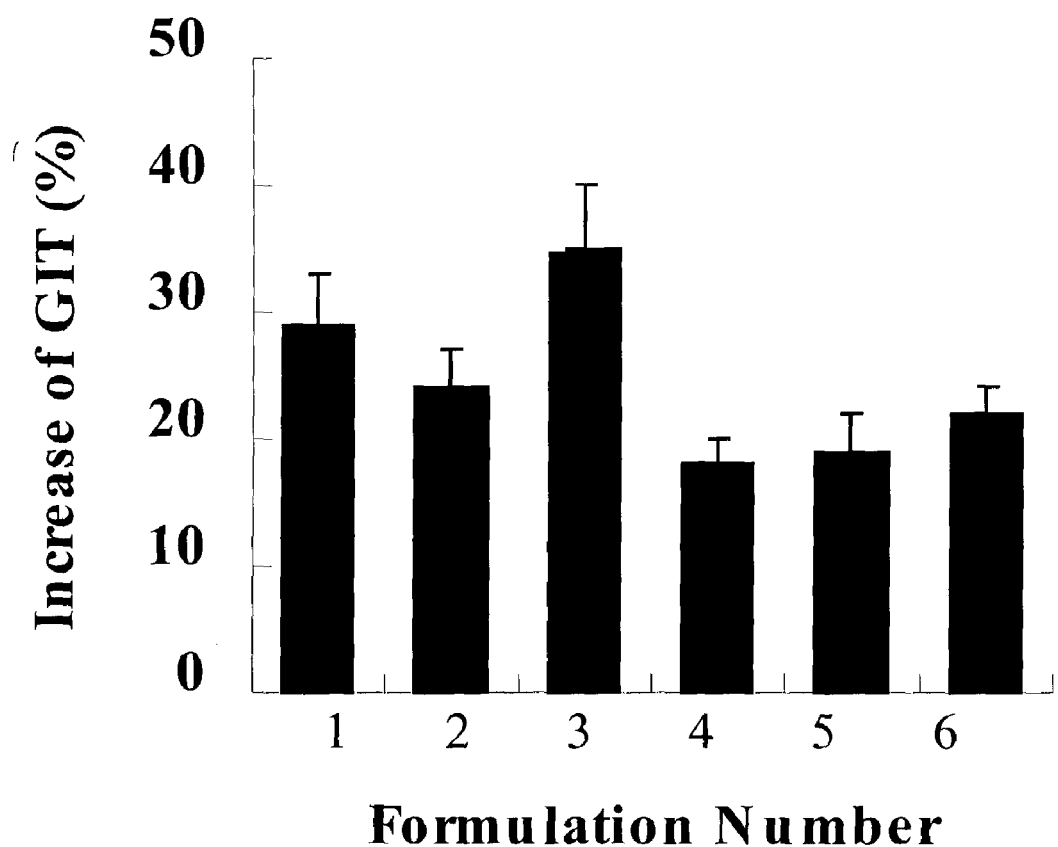
FIG. 1 shows the effects of 6 different formulations on the GIT of charcoal in mice.

Accordingly, it is an object of the present invention to provide a crude drug composition essentially comprising herbs of *Sinapis Semen Alba, Ginseng Radix* and *Zingiberis Rhizoma Siccus* for preventing and treating gastrointestinal dyskinetic diseases.

Above described *Sinapis Semen Alba* comprises a seed of *Brassica juncea*, *Ginseng Radix* comprises a root of *Panax ginseng* and *Zingiberis Rhizoma Siccus* is a dried rootstock of *Zingiber officinale*.

It is another object of the present invention to provide a crude drug composition essentially comprising herbs of *Amomi Fructus, Myristicae Semen* and *Saussureae Radix* for preventing and treating gastrointestinal dyskinetic diseases.

Above described *Amomi Fructus* is a fruit of *Amomum xanthioides*, *Myristicae Semen* is a seed of *Myristica fragrans* and *Saussureae Radix* is a root of *Saussurea lappa*.

The present invention provides a crude drug composition essentially comprising herbs of *Cyperi Rhizoma, Magnoliae Cortex, Arecae Semen, Crataegi Fructus, Atractylodes Rhizoma Alba, Agastachis Herba* and *Glycyrrhiza Radix* for preventing and treating gastrointestinal dyskinetic diseases.

Above described *Cyperi Rhizoma* is a rootstock of *Cyperus rotundus*, *Magnoliae Cortex* is a dried stem bark or a dried root bark of *Magnolia officinalis*, *Arecae Semen* is a seed of *Areca catechu*, *Crataegi Fructus* is a fruit of *Crataegus pinnatifida*, *Atractylodes Rhizoma Alba* is a rootstock of *Atractylodes macrocephala*, *Agastachis Herba* is a whole plant of *Agastache rugosa* and *Glycyrrhiza Radix* is a rootstock of *Glycyrrhiza uralensis*.

The present invention provides a crude drug composition essentially comprising herbs of *Sinapis Semen Alba*, *Ginseng Radix*, *Zingiberis Rhizoma Siccus*, *Amomi Fructus*, *Myristicae Semen* and *Saussureae Radix* for preventing and treating gastrointestinal dyskinetic diseases.

The present invention provides a crude drug composition essentially comprising herbs of *Sinapis Semen Alba*, *Ginseng Radix*, *Zingiberis Rhizoma Siccus*, *Amomi Fructus*, *Myristicae Semen*, *Saussureae Radix*, *Cyperi Rhizoma*, *Magnoliae Cortex*, *Arecae Semen*, *Crataegi Fructus*, *Atractylodes Rhizoma Alba*, *Agastachis Herba* and *Glycyrrhiza Radix* for preventing and treating gastrointestinal dyskinetic diseases.

The present invention also provides a crude drug composition additionally comprising at least one herb selected from the group consisting of *Polygonati Rhizoma*, *Artemisiae Argyi Folium*, *Forsythiae Fructus*, *Caryophylli Flos*, *Raphani Semen* and *Menthae Herba*, besides above-mentioned essential complex herbs for preventing and treating gastrointestinal dyskinetic diseases.

Above described *Polygonati Rhizoma* is a rootstock of *Polygonatum doratum*, *Artemisiae Argyi Folium* is a dried leaf of *Artemisia argyi*, *Forsythiae Fructus* is a fruit of *Forsythia koreana*, *Caryophylli Flos* is a flower of *Eugenia caryophyllata*, *Raphani Semen* is a seed of *Raphanus sativus* and *Menthae Herba* is a whole plant or a leaf of *Mentha arvensis var. piperascens*.

In accordance with one aspect of the present invention, there provided a pharmaceutical composition essentially comprising a crude drug composition of *Sinapis Semen Alba*, *Ginseng Radix* and *Zingiberis Rhizoma Siccus* and a pharmaceutically acceptable carrier thereof as an active ingredient for treating and preventing gastrointestinal dyskinetic diseases.

In accordance with another aspect of the present invention, there provided a pharmaceutical composition essentially comprising a crude drug composition of *Amomi Fructus*, *Myristicae Semen* and *Saussureae Radix* and a pharmaceutically acceptable carrier thereof as an active ingredient for treating and preventing gastrointestinal dyskinetic diseases.

In accordance with another aspect of the present invention, there provided a pharmaceutical composition essentially comprising a crude drug composition of *Cyperi Rhizoma*, *Magnoliae Cortex*, *Arecae Semen*, *Crataegi Fructus*, *Atractylodes Rhizoma Alba*, *Agastachis Herba* and *Glycyrrhiza Radix* and a pharmaceutically acceptable carrier thereof as an active ingredient for treating and preventing gastrointestinal dyskinetic diseases.

In accordance with another aspect of the present invention, there provided a pharmaceutical composition essentially comprising a crude drug composition of *Sinapis Semen Alba*, *Ginseng Radix*, *Zingiberis Rhizoma Siccus*, *Amomi Fructus*, *Myristicae Semen* and *Saussureae Radix*, preferably with a ratio of 0.5~2:0.5~2:0.5~2:0.5~2:0.5~2:0.5~2 and a pharmaceutically acceptable carrier thereof as an active ingredient for treating and preventing gastrointestinal dyskinetic diseases.

In accordance with another aspect of the present invention, there provided a pharmaceutical composition essentially comprising a crude drug composition of *Sinapis Semen Alba*, *Ginseng Radix*, *Zingiberis Rhizoma Siccus*, *Amomi Fructus*, *Myristicae Semen*, *Saussureae Radix*, *Cyperi Rhizoma*, *Magnoliae Cortex*, *Arecae Semen*, *Crataegi Fructus*, *Atractylodes Rhizoma Alba*, *Agastachis Herba*, *Glycyrrhiza Radix* and a pharmaceutically acceptable carrier thereof as an active ingredient for treating and preventing gastrointestinal dyskinetic diseases.

In accordance with still another aspect of the present invention, there provided a pharmaceutical composition additionally comprising at least one herb selected from the group consisting of *Polygonati Rhizoma*, *Artemisiae Argyi Folium*, *Forsythiae Fructus*, *Caryophylli Flos*, *Raphani Semen* and *Menthae Herba*, besides above essential complex herbs and a pharmaceutically acceptable carrier thereof as an active ingredient for preventing and treating gastrointestinal dyskinetic diseases.

The herbs, which can be used in the present invention, include the same genus plants which would be apparent to those skilled in the art and have be used for identical or similar purpose and can be substituted for the prevention and treatment of gastrointestinal dyskinetic diseases.

Inventive crude drug composition is used in the form of pulverized form thereof, extracted form therefrom or dried extract form thereof.

Above extracted form of crude drug composition can be obtained by extracting with distilled water, lower alcohols such as methanol, ethanol and the like, or the mixtures thereof, preferably water.

The pharmaceutical composition for treating gastrointestinal dyskinetic diseases could contain about 0.01 to 95 w/w %, preferably 0.5 to 80 w/w % of the above crude drug composition of present invention based on the total weight of the composition.

An inventive crude drug composition may be prepared in accordance with the following preferred embodiment.

For the present invention, above crude drug composition can be prepared by following procedure; essential herbs, i.e., *Sinapis Semen Alba*, *Ginseng Radix*, *Zingiberis Rhizoma Siccus*, *Amomi Fructus*, *Myristicae Semen*, *Saussureae Radix*, *Cyperi Rhizoma*, *Magnoliae Cortex*, *Arecae Semen*, *Crataegi Fructus*, *Atractylodes Rhizoma Alba*, *Agastachis Herba* and *Glycyrrhiza Radix* are washed, dried, mixed with proper ratio(w/w), otherwise, additional herbs such as *Polygonati Rhizoma*, *Artemisiae Argyi Folium*, *Forsythiae Fructus*, *Caryophylli Flos*, *Raphani Semen* and *Menthae Herba* can be co-mixed at the stage. Above mixture thereof is pulverized to obtain the pulverized form of crude drug composition.

Above pulverized crude drug composition is mixed with 5 to 20-fold, preferably, 10 to 15-fold volume of distilled water, alcohols such as methanol, ethanol and the like, or the mixtures thereof, preferably, distilled water or the mixture of ethanol and water; and is enfleuraged at the temperature ranging from 0 to room temperature, preferably from 4 to 6° C., for the period ranging from 12 hours to 48 hours, preferably 20 to 24 hours or heated at the temperature ranging from 80 to 100° C., preferably above 90° C., for the period ranging from 1 to 24 hours, preferably 3 to 5 hours with 2 to 5 times, or extracted by sonication, reflux or conventional extraction to obtain an aqueous extract form of crude drug composition.

Additionally, the herbal extract is filtered and concentrated at 40 to 80° C. under reduced pressure. The extract is concentrated by azeotropic distillation with volume of 10 to 60-fold water, 1 to 5 times and then dried by freeze drying or vacuum drying to obtain a dried extract form of crude drug composition.

It is another object of the present invention to provide a process for preparing crude drug composition described above for gastrointestinal dyskinetic diseases.

It is still another object of the present invention to provide a pharmaceutical composition comprising the pulverized form, extracted form or dried extract form of above crude drug composition obtained by above described process as an active ingredient for preventing and treating gastrointestinal dyskinetic diseases.

The crude drug composition comprising the mixture of pulverized *Sinapis Semen Alba, Ginseng Radix, Zingiberis Rhizoma Siccus, Amomi Fructus, Myristicae Semen, Saussureae Radix, Cyperi Rhizoma, Magnoliae Cortex, Arecae Semen, Crataegi Fructus, Atractylodes Rhizoma Alba, Agastachis Herba* and *Glycyrrhiza Radix*, prepared by above-described process was designated as PG202. Inventive PG202, the novel herb-based prokinetic agent significantly enhanced gastrointestinal motility. In the mouse model based on the propulsion of a charcoal meal through the gastrointestinal tract, PG202 at 1.0 g/kg moved the charcoal much more efficiently than either the vehicle or the commercial prokinetic, mosapride citrate. When the oral acute toxicity of PG202 was tested, PG202 had no apparent effect on mortality, clinical signs, body weight changes, and gross findings at necropsy.

The pharmaceutical composition for treating gastrointestinal dyskinetic diseases could contain about 0.01 to 95 w/w %, preferably 0.5 to 80 w/w % of the above crude drug composition of present invention based on the total weight of the composition.

In accordance with the present invention, there provided a crude drug composition which can add or remove properly another herbs and increase or decrease composition ratio of herbs for keeping an effective therapeutic activity against gastrointestinal dyskinetic diseases.

The crude drug composition of the present invention has potent prokinetic activity and the pharmaceutical composition of the present invention thus may be employed for treating gastrointestinal dyskinetic diseases selected at least one from the group consisting of early satiety, aneilema and bloating symptom, related to functional dyspepsia, constipation, irritable bowel syndrome, enterocleisis, gastrointestinal dyskinesia caused by diabetes, chemotherapy or myotonic dystrophy.

It is another of the present invention to provide a prokinetic agent comprising the above crude drug composition as an active ingredient in an amount effective to preventing and treating gastrointestinal dyskinetic diseases.

It is another of the present invention to provide a use of the inventive crude drug composition for the preparation of a medicament such as a prokinetic agent for preventing or treating gastrointestinal dyskinetic diseases It is another of the present invention to provide a method of treating of gastrointestinal dyskinetic diseases in a mammal comprising administering to said mammal an effective amount of crude drug composition and pharmaceutically acceptable carrier thereof.

It is another of the present invention to provide a method for alleviating early satiety, aneilema and bloating symptom, related to functional dyspepsia, constipation, irritable bowel syndrome, enterocleisis, gastrointestinal dyskinesia caused by diabetes, chemotherapy or myotonic dystrophy in a mammal comprising administering to said mammal an effective amount of the crude drug composition and pharmaceutically acceptable carrier thereof.

The crude drug composition of the present invention has potent prokinetic activity and the pharmaceutical composition of the present invention thus may be employed for treating gastrointestinal dyskinetic diseases selected at least one from the group consisting of early satiety, aneilema and bloating symptom, related to functional dyspepsia, constipation, irritable bowel syndrome, enterocleisis, gastrointestinal dyskinesia caused by diabetes, chemotherapy or myotonic dystrophy.

The inventive composition may additionally comprise conventional carrier, adjuvants or diluents in accordance with a using method. It is preferable that said carrier is used as appropriate substance according to the usage and application method, but it is not limited. Appropriate diluents are listed in the written text of Remington's Pharmaceutical Science (Mack Publishing co, Easton Pa.).

Hereinafter, the following formulation methods and excipients are merely exemplary and in no way limit the invention.

The crude drug composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

Pharmaceutical formulations containing crude drug composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), suppository, or sterile injectable preparation (solution, suspension, emulsion).

The crude drug composition of the present invention in pharmaceutical dosage forms may be used in the form of their pharmaceutically acceptable salts, and also may be used alone or in appropriate association, as well as in combination with other pharmaceutically active compounds.

The desirable dose of the inventive composition varies depending on the condition and the weight of the subject, severity, drug form, route and period of administration, and may be chosen by those skilled in the art. However, in order to obtain desirable effects, it is generally recommended to administer at the amount ranging 0.01–10 g/kg, preferably, 1 to 5 g/kg by weight/day of the inventive composition of the present invention. The dose may be administered in a single or multiple doses per day. In terms of composition, the crude drug composition should be present between 0.01 to 80% by weight, preferably 0.5 to 50% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

Accordingly, it is another object of the present invention to provide a health food comprising a crude drug composition.

The present invention provides a health food essentially comprising a crude drug composition of *Sinapis Semen Alba*, *Ginseng Radix* and *Zingiberis Rhizoma Siccus* and a sitologically acceptable additive to prevent and improve gastrointestinal dyskinetic diseases.

The present invention provides a health food essentially comprising a crude drug composition of *Amomi Fructus*, *Myristicae Semen* and *Saussureae Radix* and a sitologically acceptable additive to prevent and improve gastrointestinal dyskinetic diseases.

The present invention provides a health food essentially comprising a crude drug composition of *Cyperi Rhizoma*, *Magnoliae Cortex*, *Arecae Semen*, *Crataegi Fructus*, *Atractylodes Rhizoma Alba*, *Agastachis Herba* and *Glycyrrhiza Radix* and a sitologically acceptable additive to prevent and improve gastrointestinal dyskinetic diseases.

The present invention provides a health food essentially comprising a crude drug composition of *Sinapis Semen Alba*, *Ginseng Radix*, *Zingiberis Rhizoma Siccus*, *Amomi Fructus*, *Myristicae Semen* and *Saussureae Radix*, preferably with a ratio of 0.5~2:0.5~2:0.5~2:0.5~2:0.5~2:0.5~2 and a sitologically acceptable additive to prevent and improve gastrointestinal dyskinetic diseases.

The present invention provides a health food essentially comprising crude drug composition of *Sinapis Semen Alba*, *Ginseng Radix*, *Zingiberis Rhizoma Siccus*, *Amomi Fructus*, *Myristicae Semen*, *Saussureae Radix*, *Cyperi Rhizoma*, *Magnoliae Cortex*, *Arecae Semen*, *Crataegi Fructus*, *Atractylodes Rhizoma Alba*, *Agastachis Herba* and *Glycyrrhiza Radix* and a sitologically acceptable additive to prevent and improve gastrointestinal dyskinetic diseases.

The present invention provides a health food additionally comprising at least one herb selected from the group consisting of *Polygonati Rhizoma*, *Artemisiae Argyi Folium*, *Forsythiae Fructus*, *Caryophylli Flos*, *Raphani Semen* and *Menthae Herba*, besides above essential crude drug composition and a sitologically acceptable additive to prevent and improve gastrointestinal dyskinetic diseases.

The crude drug composition of inventive health food is used in the form of pulverized form thereof, extracted form therefrom or dried extract form thereof.

The health food composition for preventing and improving gastrointestinal dyskinetic diseases could contain about 0.01 to 95 w/w %, preferably 0.5 to 80 w/w % of the above crude drug composition of present invention based on the total weight of the composition.

Above described the crude drug composition therein can be added to food, additive or beverage for prevention and improvement of gastrointestinal dyskinetic diseases. For the purpose of preventing and improving gastrointestinal dyskinetic diseases, wherein, the amount of above described crude drug composition in food or beverage may generally range from about 0.1 to 15 w/w %, preferably 1 to 10 w/w % of total weight of food for the health food composition and 1 to 30 g, preferably 3 to 10 g on the ratio of 100 ml of the health beverage composition.

Providing that the health beverage composition of present invention contains above described crude drug composition as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 ml of present beverage composition.

The other components than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition.

Examples of addable food comprising aforementioned crude drug composition therein are various food, beverage, gum, vitamin complex, health improving food and the like.

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

The following Examples and Experimental Examples are intended to further illustrate the present invention without limiting its scope.

Example 1

Preparation of Crude Drug Composition: Development of PG202 Formulation

All herbs used were purchased from the Kyungdong herb market (Seoul, Korea). Each herb, of which moisture was less than 10% of weight, was air-dried and minced by a grinder (RT-05, Rong Tong Iron Works, Taiwan) into brown powder.

All herbs, i.e. *Sinapis Semen Alba*, *Ginseng Radix*, *Zingiberis Rhizoma Siccus*, *Amomi Fructus*, *Myristicae Semen*, *Saussureae Radix*, *Polygonati Rhizoma*, *Artemisiae Argyi Folium*, *Forsythiae Fructus*, *Caryophylli Flos*, *Cyperi Rhizoma*, *Magnoliae Cortex*, *Arecae Semen*, *Crataegi Fructus*, *Atractylodes Rhizoma Alba*, *Agastachis Herba*, *Glycyrrhiza Radix*, *Raphani Semen* and *Menthae Herba*, were classified into five groups based on the disclosure in Chinese Medicine Books (Table 1). And to determine specific effective composition thereof, 6 different formulations in combination with above 5 groups were prepared by mixed with the same quantity of each herb according to Table 2.

TABLE 1

Composition of herbs that are contained in each group

| Group No. | Herbs Incorporated |
|---|---|
| 1 | Sinapis Semen Alba, Ginseng Radix, Zingiberis Rhizoma Siccus |
| 2 | Amomi Fructus, Myristicae Semen, Saussureae Radix |
| 3 | Polygonati Rhizoma, Artemisiae Argyi Folium, Forsythiae Fructus, Caryophylli Flos |
| 4 | Cyperi Rhizoma, Magnoliae Cortex, Arecae Semen, Crataegi Fructus, Atractylodes Rhizoma Alba, Agastachis Herba, Glycyrrhiza Radix |
| 5 | Raphani Semen, Menthae Herba |

TABLE 2

Composition of formulations & herbs that are contained in each group

| Formulation No. | Groups of Herbs Incorporated |
|---|---|
| 1 | Group1, Group4 |
| 2 | Group2, Group4 |
| 3 | Group1, Group2, Group4 |
| 4 | Group3, Group4 |
| 5 | Group3, Group4, Group5 |
| 6 | Group2, Group3, Group4, Group5 |

(1-1) Preparation of Crude Drug Composition of Formulation 1

Powder of complex herbs of formulation 1 (*Sinapis Semen Alba, Ginseng Radix, Zingiberis Rhizoma Siccus, Cyperi Rhizoma, Magnoliae Cortex, Arecae Semen, Crataegi Fructus, Atractylodes Rhizoma Alba, Agastachis Herba* and *Glycyrrhiza Radix*) was pulverized by a grinder (RT-05, Rong Tong Iron Works, Taiwan) into brown powder. Inventive crude drug composition was obtained and used as a test sample in Experimental Example 1.

(1-2) Preparation of Crude Drug Composition of Formulation 2

Powder of crude drug composition of formulation 2 (*Amomi Fructus, Myristicae Semen, Saussureae Radix, Cyperi Rhizoma, Magnoliae Cortex, Arecae Semen, Crataegi Fructus, Atractylodes Rhizoma Alba, Agastachis Herba* and *Glycyrrhiza Radix*) was prepared by the same method described in Example (1-1) and was used as a test sample in Experimental Example 1.

(1-3) Preparation of Crude Drug Composition of Formulation 3

Powder of crude drug composition of formulation 3 (*Sinapis Semen Alba, Ginseng Radix, Zingiberis Rhizoma Siccus, Amomi Fructus, Myristicae Semen, Saussureae Radix, Cyperi Rhizoma, Magnoliae Cortex, Arecae Semen, Crataegi Fructus, Atractylodes Rhizoma Alba, Agastachis Herba* and *Glycyrrhiza Radix*) was prepared by the same method described in Example (1-1) and was used as a test sample in Experimental Example 1.

(1-4) Preparation of Crude Drug Composition of Formulation 4

Powder of crude drug composition of formulation 4 (*Polygonati Rhizoma, Artemisiae Argyi Folium, Forsythiae Fructus, Caryophylli Flos, Magnoliae Cortex, Arecae Semen, Crataegi Fructus, Atractylodes Rhizoma Alba, Agastachis Herba* and *Glycyrrhiza Radix*) was prepared by the same method described in Example (1-1) and was used as a test sample in Experimental Example 1.

(1-5) Preparation of Crude Drug Composition of Formulation 5

Powder of crude drug composition of formulation 5 (*Polygonati Rhizoma, Artemisiae Argyi Folium, Forsythiae Fructus, Caryophylli Flos, Magnoliae Cortex, Arecae Semen, Crataegi Fructus, Atractylodes Rhizoma Alba, Agastachis Herba* and *Glycyrrhiza Radix, Raphani Semen, Menthae Herba*) was prepared by the same method described in Example (1-1) and was used as a test sample in Experimental Example 1.

(1-6) Preparation of Crude Drug Composition of Formulation 6

Powder of crude drug composition of formulation 6 (*Amomi Fructus, Myristicae Semen, Saussureae Radix, Polygonati Rhizoma, Artemisiae Argyi Folium, Forsythiae Fructus, Caryophylli Flos, Magnoliae Cortex, Arecae Semen, Crataegi Fructus, Atractylodes Rhizoma Alba, Agastachis Herba* and *Glycyrrhiza Radix, Raphani Semen, Menthae Herba*) was prepared by the same method described in Example (1-1) and was used as a test sample in Experimental Example 1.

Experimental Example 1

Estimation of Gastrointestinal Motility

Female ICR derived mice (Seoul National University) weighing 22±2 grams were used. All animals were maintained in a controlled environment with temperatures at 22° C.–24° C. and humidity at 60%–80% with 12 hours of light and dark cycles for at least one week prior to use. 9 groups of 8 ICR derived female mice were fasted with free access to water for 16 hours prior to testing.

For the estimation of the effect on gastrointestinal motility, 0.1 g of the brown powder of each formulation obtained in Example 1, was dissolved in 1 ml of 2% Tween 80 (Wako, Japan) and administrated orally to the mice.

Atropine sulfate (Sigma, USA) was used for the negative control in the experiment, which is known to induce smooth muscle relaxation. Mosapride citrate was administered at 20 mg/kg. Each crude drug composition of 6 formulations prepared in Example 1, was administered at 1.0 g/kg. At 60 minutes post dosing, the animals were given a suspension of 5% activated charcoal (Sigma, USA) in a 10% arabic gum (Sigma, USA) solution (0.3 ml/animal p.o.) and sacrificed 15 minutes later.

Charcoal is a nontoxic substance with non-pharmacological activity.

The intestine was removed and the length of the gut in cm (GL) as well as distance of charcoal movement from the pylorus to the beginning of the charcoal column in cm (CP), was measured. Gastrointestinal transit (GIT) has been calculated as below Formula 1. The mean GIT value of each group has been compared to that of the vehicle control.

$$GIT(\%) = (CP/GL) \times 100 \qquad \text{Formula 1}$$

Values were expressed as means±S.E.M. Students' t-test was used for the statistical analysis of the results of gastrointestinal transit. Probability values (p) less than 0.05 were considered to be significant.

The highest GIT value was showed in the group administered with formulation 3 prepared in Example (1-3) and the next one was with formulation 1, formulation 2, formulation 6, formulation 5 and formulation 4 in that order (FIG. 1).

The formulation 3 and formulation 1, which have the higher GIT, include the herbs of group 1 and group 4 and the formulation 6 includes all of the above-mentioned herbs excepting the herbs of group 1. Besides, formulation 2, 3 and 6, which include the herbs of group 2 in common, show the great increase of GIT.

Therefore, it could be deduced that herbs of group 1 and group 2 was effective to activate gastrointestinal motility.

The formulation 3, designated as PG202, which showed excellent gastrointestinal prokinetic effect, was used as a test sample in the following Experimental Examples.

Experimental Example 2

Dosage-Dependent Effects of PG202 on the GIT

To estimate the dosage dependent effect of PG202 on gastrointestinal motility, the PG202 was administrated orally to the mice.

PG202, prepared in Example 1, was administered into the mice orally at concentrations of 0.1 g/kg, 1.0 g/kg, and 5.0 g/kg. The control group was administered with the vehicle (2% Tween 80) at 10 ml/kg. At 60 minutes post dosing, the animals were given a suspension of 5% activated charcoal (Sigma, USA) in a 10% Arabic gum (Sigma, USA) solution (0.3 ml/animal p.o.) and sacrificed 15 minutes later and the gastrointestinal transit (GIT) was examined according to the Formula 1. Data have been expressed as means±S.E.M.*p<0.05.

Figure 2:
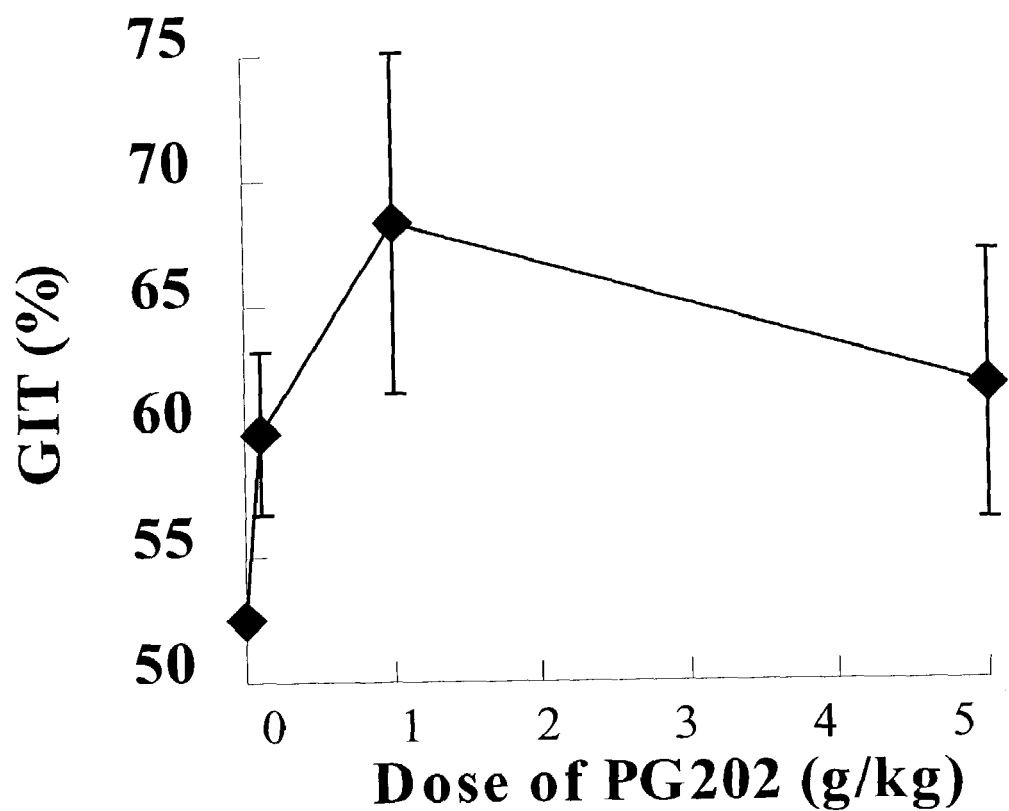
FIG. 2 shows the dose-dependent effects of PG202 on the GIT of charcoal in mice.

In the result, GIT was 52.6±2.0 in the control group treated with the vehicle (2% Tween 80 solution) alone. PG202 significantly increased GIT compared to the control group and the prokinetic effect of PG202 was dose dependent (FIG. 2). At 0.1 g/kg, GIT (59.9±3.2) was increased by 17% compared to the control. It reached its' highest peak at 1.0 g/kg with the increase of GIT (68.3±6.8) by 30%, and decreased at a higher concentration of 5.0 g/kg.

This indicated that there might be an optimum concentration for PG202 as a prokinetic agent.

Experimental Example 3

Effects of PG202 and Commercial Prokinetic Agent

In this experiment, the effect of PG202 was compared with that of commercially available Mosapride citrate and Atropine sulfate on gastrointestinal motility.

PG202 was administered orally at 1.0 g/kg to the test group, 2% Tween 80 (Wako, Japan) at 10 ml/kg to control group, Mosapride citrate at 20 mg/kg to positive control group, Atropine sulfate (Sigma, USA) at 100 mg/kg to negative control group. Data have been expressed as means±S.E.M.*p<0.05.

At 60 minutes post dosing, the animals were given a suspension of 5% activated charcoal (Sigma, USA) in a 10% arabic gum (Sigma, USA) solution (0.3 ml /animal p.o.) and sacrificed 15 minutes later. GIT (%) values were determined according to the Formula 1.

In the result, the percentage of the increase of GIT compared to the control group was calculated. PG202 at 1.0 g/kg increased the GIT (68.3±6.8) by 30% and mosapride citrate at 20 mg/kg increased the GIT by 21% (63.7±5.2) respectively, as compared to the control. Atropine decreased the GIT (35.4±3.4) by 35% at the concentration of 100 mg/kg in comparison to the control group.

Figure 3:
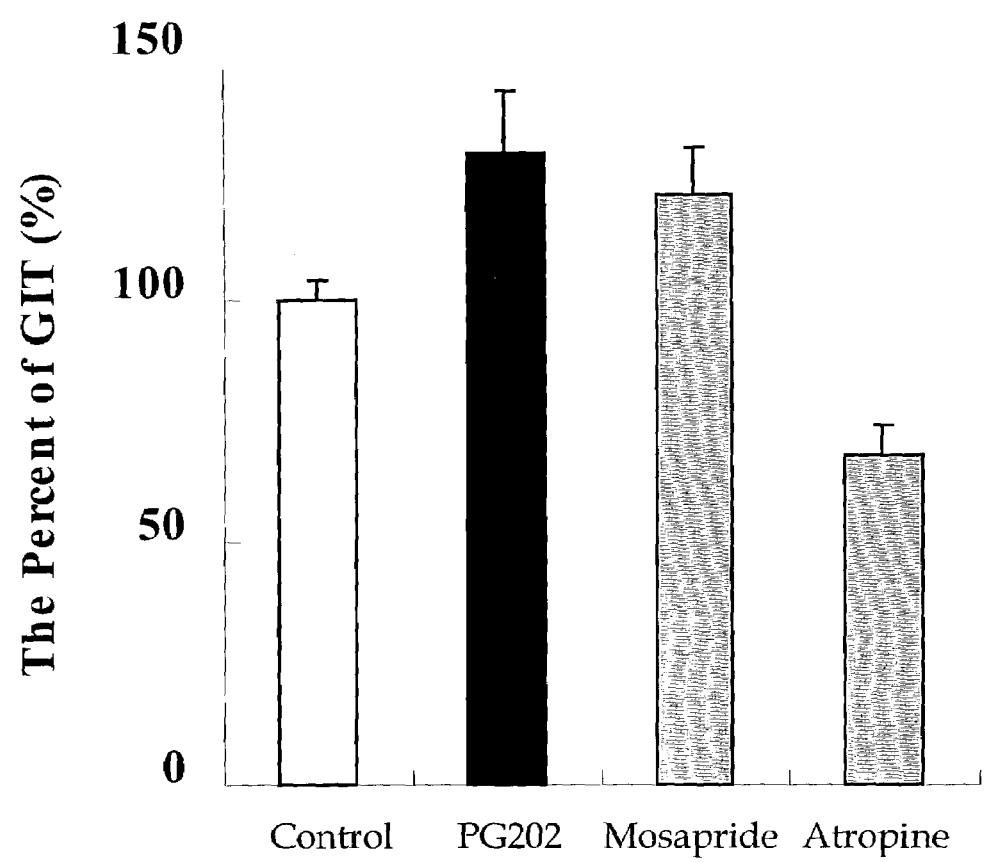
FIG. 3 represents the effects of PG202 and mosapride citrate on the GIT of charcoal in mice.

At 1.0 g/kg, PG202 increased GIT of charcoal meal transfer from the pylorus in mouse intestine compared to the control and it was also more effective than the commercial prokinetic agent, mosapride citrate (FIG. 3).

Experimental Example 4

Evaluation of 5-$HT_3$ Agonistic Activity

Effect of PG202 (n=3) on the contraction of isolated guinea pig ileum was tested. The segment of ileum obtained from Duncan Hartley was derived from male or female guinea pigs weighing 325±25 g and which was sacrificed by $CO_2$ overexposure. The tissue was placed under 1 g tension in a 10 ml bath containing Krebs solution pH 7.4 at 32° C. Test sample-induced isotonically recorded contraction within 5 min, comparing with the control 2.6M serotonin (5-HT) response, suggests as a possible serotonin 5-$HT_3$ receptor agonist activity. Concentration-response curves were constructed in a cumulative manner. Each point represents the mean±S.E.M.

Figure 4:
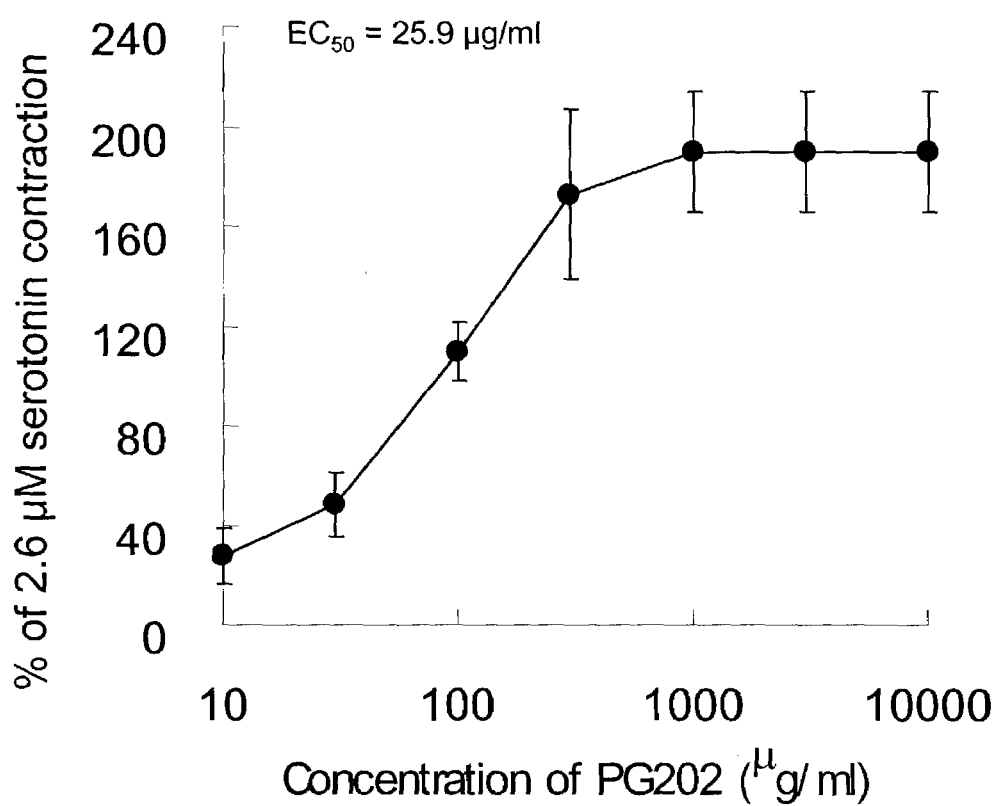
FIG. 4 represents the effect of PG202 on contraction by activation of $5-HT_3$ receptor (% contraction compared with 5-HT)

As shown in FIG. 4, the results demonstrated that the increase of PG202 augmented the contraction of ileum tissue by 189% ($EC_{50}$=25.9 μg/ml).

Experimental Example 5

Evaluation of 5-$HT_4$ Agonistic Activity

Effect of PG202 (n=3) on the relaxation of carbachol-induced contraction of isolated rat esophagus was tested. A segment of esophagus obtained from Wistar was derived from male or female rats weighing 270±25 g which was sacrificed by $CO_2$ overexposure. The tissue was placed under 1 g tension in a 10 ml bath containing 3M indomethacin and 1M ketanserin in Krebs solution pH 7.4 at 32° C. and submaximal tonic isometrically recorded contraction was induced by carbachol (1 μM). Test substance-induced relaxation within 5 min, comparing with the control 0.3M serotonin (5-HT) response, suggests as a possible serotonin 5-$HT_4$ receptor agonist activity. Concentration-response curves were constructed in a cumulative manner. Each point represents the mean±S.E.M.

Figure 5:
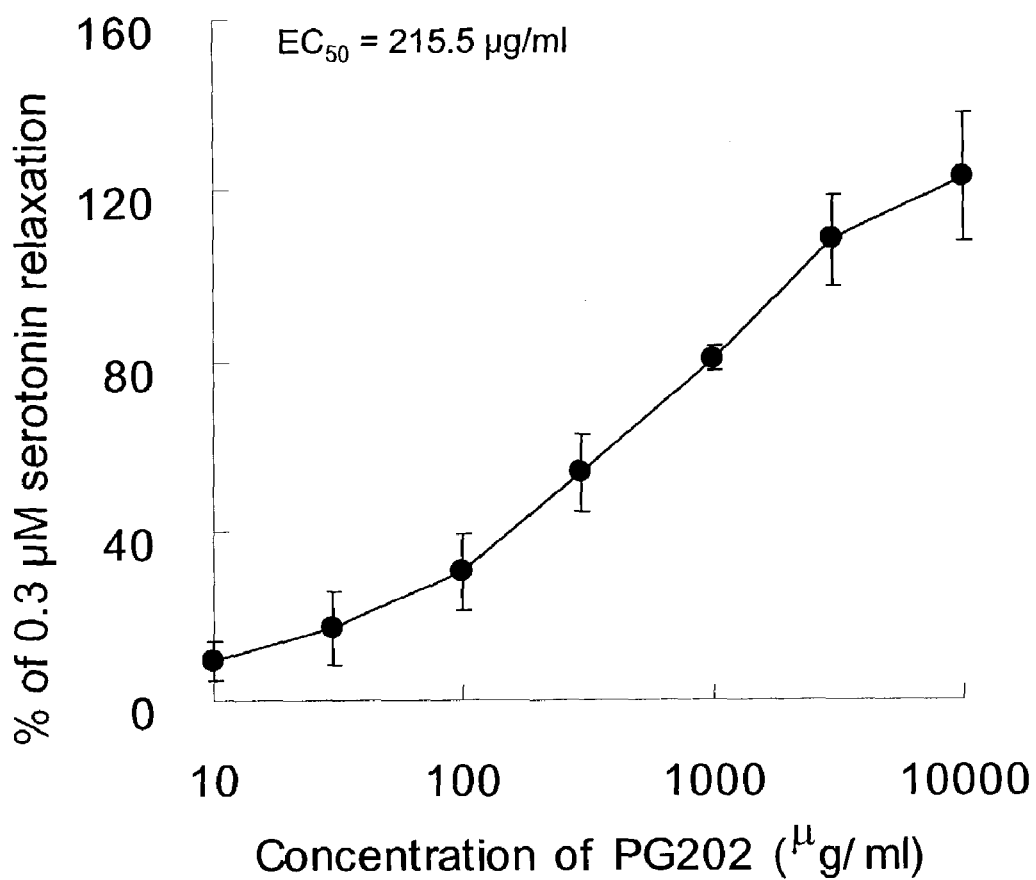
FIG. 5 represents the effect of PG202 on relaxation by activation of $5-HT_4$ receptor (% relaxation compared with 5-HT).

As shown in FIG. 5, the results demonstrated that the increase of PG202 augmented the relaxation of esophagus tissue by 123% ($EC_{50}$=215.5 μg/ml).

Experimental Example 6

Evaluation of Acute Toxicity

Twelve male SPF Sprague-Dawley rats ranging from 72.7 to 82.4 g, were obtained at the age of 4 weeks and acclimatized for 7 days. Additionally, 12 female SD rats ranging from 75.4 to 82.3 g, were obtained and acclimatized. Separately, 10 healthy male and female rats were selected on the day of treatment and used in the study. PG202 was resuspended at 250 mg/ml and administrated at 20 ml/kg. To study the effects of administration volume itself, we had a negative control group with 20 ml/kg of sterilized distilled water. The animals were fasted overnight before the treatment. PG202 was administered orally by gavage. Following administration, animals were further fasted for 3–4 hours. Mortality and clinical signs were checked 1, 2, 3, 4, 5 and 6 hours after dosing and then once a day thereafter until day 14. Individual body weights of animals were measured shortly before the test item administration and on days 1, 3, 7 and 14 following the treatment. On the 14th day following treatment, all animals were anesthetized by overdose of carbon dioxide and necropsied with special attention to all vital organs.

Hereinafter, the formulating methods and kinds of excipients will be described, but the present invention is not limited to them. The representative preparation examples were described as follows.

| Preparation of injection | |
|---|---|
| PG202 | 100 mg |
| Sodium metabisulfite | 3.0 mg |
| Methyl paraben | 0.8 mg |
| Propyl paraben | 0.1 mg |
| Distilled water for injection | optimum amount |

Injection preparation was prepared by dissolving active component, controlling pH to about 7.5 and then filling all the components in 2 ml ample and sterilizing by conventional injection preparation method.

| Preparation of powder | |
|---|---|
| PG202 | 500 mg |
| Corn Starch | 100 mg |
| Lactose | 100 mg |
| Talc | 10 mg |

Powder preparation was prepared by mixing above components and filling sealed package.

| Preparation of tablet | |
|---|---|
| PG202 | 200 mg |
| Corn Starch | 100 mg |
| Lactose | 100 mg |
| Magnesium stearate | optimum amount |

Tablet preparation was prepared by mixing above components and entabletting.

| Preparation of capsule | |
|---|---|
| PG202 | 100 mg |
| Lactose | 50 mg |
| Corn starch | 50 mg |
| Talc | 2 mg |
| Magnesium stearate | optimum amount |

Tablet preparation was prepared by mixing above components and filling gelatin capsule by conventional gelatin preparation method.

| Preparation of liquid | |
|---|---|
| PG202 | 1000 mg |
| Sugar | 20 g |
| Polysaccharide | 20 g |
| Lemon flavor | 20 g |

Liquid preparation was prepared by dissolving active component, and then filling all the components in 1000 ml ample and sterilizing by conventional liquid preparation method.

| Preparation of health food | |
|---|---|
| PG202 | 1000 mg |
| Vitamin mixture | optimum amount |
| Vitamin A acetate | 70 μg |
| Vitamin E | 1.0 mg |
| Vitamin B$_1$ | 0.13 mg |
| Vitamin B$_2$ | 0.15 mg |
| Vitamin B6 | 0.5 mg |
| Vitamin B12 | 0.2 μg |
| Vitamin C | 10 mg |
| Biotin | 10 μg |
| Amide nicotinic acid | 1.7 mg |
| Folic acid | 50 μg |
| Calcium pantothenic acid | 0.5 mg |
| Mineral mixture | optimum amount |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

The above mentioned vitamin and mineral mixture may be varied in many ways. Such variations are not to be regarded as a departure from the spirit and scope of the present invention.

| Preparation of health beverage | |
|---|---|
| PG202 | 1000 mg |
| Citric acid | 1000 mg |
| Oligosaccharide | 100 g |
| Apricot concentration | 2 g |
| Taurine | 1 g |
| Distilled water | 900 ml |

Health beverage preparation was prepared by dissolving active component, mixing, stirred at 85° C. for 1 hour, filtered and then filling all the components in 1000 ml ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the crude drug composition-based pharmaceutical compositions can alleviate the gastrointestinal dyskinetic symptoms and enhance the upper gastrointestinal mobility.

The crude drug compositions according to the present invention are useful in the prevention and treatment of the gastrointestinal dyskinetic diseases and can be used as safe and efficient prokinetic agent.

What is claimed is:

1. A pharmaceutical composition comprising a mixture of herbal extracts from: *Sinapis Semen Alba, Ginseng Radix, Zingiberis Rhizome Siccus, Amomi Fructus, Myristicae Semen, Saussureae Radix, Cyperi Rhizome, Magnoliae Cortex, Arecae Semen, Crataegi Fructus, Atractylodes Rhizome Alba, Agastachis Herba*, and *Glycyrrhiza Radix* as the active ingredient and a pharmaceutically acceptable carrier for treating gastrointestinal dyskinetic diseases.

2. The pharmaceutical composition of claim 1, wherein the extracts from *Sinapis Semen Alba, Ginseng Radix. Zingiberis Rhizome Slows, Amomi Fructus, Myristicae Semen, Saussureae Radix* are present in a ratio of 0.5–2:0.5–2:0.5–2:0.5–2:0.5–2:0.5–2.

3. The pharmaceutical composition of claim 1, wherein the mixture of herbal extracts is in the form of a pulverized form, an extracted form or a dried extract form.

4. The pharmaceutical composition of claim 3, wherein the pulverized form, the extracted form or the dried extract form is extracted with an extract solvent selected from the group consisting of distilled water, lower alcohol and mixtures thereof.

5. The pharmaceutical composition of claim 1, wherein the mixture of herbal extracts is about 0.01 to 95 w/w % based on the total weight of the composition.

6. The pharmaceutical composition of claim 1, wherein said gastrointestinal dyskinetic diseases are selected from the group consisting of early satiety, aneilema and bloating symptom, related to functional dyspepsia, constipation, irritable bowel syndrome, enterocleisis gastrointestinal dyskinesia caused by diabetes, chemotherapy or myotonic dystrophy.

7. The pharmaceutical composition of claim 1, wherein said acceptable carrier is formulated from one of the group consisting of a powder, granule, tablet, capsule, suspension, emulsion, syrup, aerosol, topical medicine suppository or sterile injection.

8. A health food consisting essentially of a mixture of herbal extracts from *Sinapis Semen Alba, Ginseng Radix* and *Zingiberis Rhizome Siccus* and a sitologically acceptable additive to improve gastrointestinal dyskinetic diseases.

9. A health food consisting essentially of a mixture of herbal extracts from *Amomi Fructus, Myristicae Semen* and *Saussureae Radix* and a sitologically acceptable additive to improve gastrointestinal dyskinetic diseases.

10. A health food consisting essentially of a mixture of herbal extracts from *Sinapis Semen Alba, Ginseng Radix, Zingiberis Rhizome Siccus, Amomi Fructus, Myristicae Semen, Saussureae Radix, Cyperi Rhizome, Magnoliae Cortex, Arecae Semen, Crataegi Fructus, Atractylodes Rhizome Alba, Agastachis Herba* and *Glycyrrhiza Radix* and a sitologically acceptable additive to improve gastrointestinal dyskinetic diseases.

11. The health food of claim 8, wherein the mixture of herbal extracts is in the form of a pulverized form, an extracted form, or a dried extract form.

12. The health food of claim 8, wherein said health food is provided as powder, granule, tablet, capsule or beverage type.

13. A prokinetic agent comprising the mixture of herbal extracts as set forth in claim 1 as an active ingredient in an amount effective to treating gastrointestinal dyskinetic diseases.

14. A method of treating gastrointestinal dyskinetic diseases in a mammal comprising administering to said mammal an effective amount of the mixture of herbal extracts as set forth in claim 1 and a pharmaceutically acceptable carrier thereof.

* * * * *